United States Patent [19]

Rao

[11] Patent Number: 5,545,770
[45] Date of Patent: *Aug. 13, 1996

[54] PROCESS FOR MANUFACTURE OF HIGH PURITY 1, 1-DICHLOROTETRAFLUOROETHANE

[75] Inventor: V. N. Mallikarjuna Rao, Wilmington, Del.

[73] Assignee: E.I. Du Pont de Nemours and Company, Wilmington, Del.

[ * ] Notice: The term of this patent shall not extend beyond the expiration date of Pat. No. 5,446,216.

[21] Appl. No.: 437,195

[22] Filed: May 8, 1995

Related U.S. Application Data

[63] Continuation of Ser. No. 146,335, Nov. 1, 1993, abandoned.

[51] Int. Cl.$^6$ .......................... C07C 19/08; C07C 17/08
[52] U.S. Cl. ........................ 570/151; 570/165; 570/167; 570/169; 570/176
[58] Field of Search ............................. 570/151, 165, 570/169, 167, 176

[56] References Cited

U.S. PATENT DOCUMENTS

| | | | |
|---|---|---|---|
| 2,478,362 | 8/1949 | Benning | 202/51 |
| 2,598,411 | 5/1952 | Miller et al. | 260/653 |
| 3,157,707 | 11/1964 | Clark et al. | 570/169 |
| 3,632,834 | 1/1972 | Christoph | 260/653.7 |
| 4,925,993 | 5/1990 | Zawalski | 570/151 |
| 5,017,732 | 5/1991 | Zawalski . | |
| 5,055,624 | 10/1991 | Lantz et al. | 570/67 |
| 5,136,113 | 8/1992 | Rao | 570/176 |
| 5,243,106 | 9/1993 | Manzer et al. | 570/166 |
| 5,243,108 | 9/1993 | Manzer et al. | 570/166 |

FOREIGN PATENT DOCUMENTS

| | | | |
|---|---|---|---|
| 0317981 | 5/1989 | European Pat. Off. | 570/151 |
| 0347830 | 12/1989 | European Pat. Off. | 570/176 |
| 0426343 | 5/1991 | European Pat. Off. . | |
| WO91/105752 | 5/1991 | WIPO . | |
| WO94/03417 | 2/1994 | WIPO . | |
| WO95/12565 | 9/1994 | WIPO . | |
| WO95/12564 | 5/1995 | WIPO . | |

OTHER PUBLICATIONS

Gervasutti, C. et al., *J. Fluorine Chem.*, 19, 1–20, 1981/82.

Bitner, J. L. et al, *U.S. Dept. Comm. Off. Tech. Serv. Rep.* 136732, 25–27, 1958.

*Primary Examiner*—Alan Siegel

[57] ABSTRACT

A process is disclosed for producing a product comprising $CCl_2FCF_3$ substantially free of $CClF_2CClF_2$. The process includes (i) contacting a mixture of perhalogenated hydrocarbons which is essentially free of $CClF_2CClF_2$ and comprises from 20 to 80 mole percent $CCl_3CF_3$ and from 5 to 80 mole percent total of at least one compound selected from the group consisting of $CCl_2=CCl_2$, $CCl_3CCl_2F$, $CCl_2FCCl_2F$ and $CClF_2CCl_3$ with HF and optionally $Cl_2$ (provided that when the mixture comprises $CCl_2=CCl_2$, $Cl_2$ is supplied in a mole ratio of $Cl_2$ to $CCl_2=CCl_2$ of at least 1:2) over a fluorination catalyst at an elevated temperature no higher than 375° C., to provide a product mixture comprising $CCl_2FCClF_2$ and $C_2Cl_2F_4$ wherein the ratio of $CClF_2CClF_2$ to $CCl_2FCF_3$ is less than about 1:50; (ii) recovering said $C_2Cl_2F_4$ from the product mixture; (iii) isomerizing $CCl_2FCClF_2$ from the product mixture to $CCl_3CF_3$ in the presence of an isomerization catalyst; and (iv) recycling the $CCl_3CF_3$ produced by the isomerization of step (iii) to step (i). The process may be used to produce high purity $CH_2FCF_3$ when combined with the hydrodehalogenation of the high purity $CCl_2FCF_3$ from step (ii) in the presence of HF.

19 Claims, No Drawings

PROCESS FOR MANUFACTURE OF HIGH PURITY 1,1-DICHLOROTETRAFLUOROETHANE

This is a continuation of application Ser. No. 08/146,335, filed Nov. 1, 1993, now abandoned.

FIELD OF THE INVENTION

This invention relates to a process for the manufacture of 1,1-dichlorotetrafluoroethane (i.e., $CF_3CCl_2F$ or CFC-114a) and more particularly to a process for the manufacture of CFC-114a substantially free of its isomer 1,2-dichlorotetrafluoroethane (i.e., $CClF_2CClF_2$ or CFC-114).

BACKGROUND 1,1-Dichlorotetrafluoroethane is of interest as an intermediate to 1,1,1,2-tetrafluoroethane (i.e., $CF_3CH_2F$ or HFC-134a) which can be obtained via catalytic hydrogenolysis of its carbon-chlorine bonds using a supported metal hydrogenation catalyst (see e.g., C. Gervasutti et al., J. Fluorine Chem., 1981/82, 19, pgs. 1–20). HFC-134a is an environmentally acceptable potential replacement for chlorofluorocarbon (i.e., CFC) refrigerants, blowing agents, aerosol propellants and sterilants that are being viewed with concern in connection with the destruction of stratospheric ozone. It is highly desired that the 1,1-dichlorotetrafluoroethane employed in the hydrogenolysis route to HFC-134a has as low a content of 1,2-dichlorotetrafluoroethane as practicable since the presence of CFC-114 during hydrogenolysis can lead to formation of 1,1,2,2-tetrafluoroethane (i.e., $CHF_2CHF_2$ or HFC-134; see e.g., J. L. Bitner et al., U.S. Dep. Comm. Off. Tech. Serv. Rep. 136732, (1958), p. 25). HFC-134 mixed in HFC-134a may be objectionable for some applications depending on concentration and, since the two isomers boil only 7° C. apart, separation of the isomers in high purity is difficult.

Commercial processes for producing $C_2Cl_2F_4$ using either chlorofluorination of $C_2Cl_4$ or fluorination of $C_2Cl_6$ typically yield CFC-114 as the major isomer with CFC-114a as a minor component. Also, the precursor of CFC-114a, 1,1,1-trichlorotrifluoroethane (i.e., $CCl_3CF_3$ or CFC-113a) is typically produced as a minor component when its isomer, 1,1,2-trichlorotrifluoroethane (i.e., $CClF_2CCl_2F$ or CFC-113) is manufactured using similar processes. For example, one well-known and widely-used route to the trichlorotrifluoroethanes and dichlorotetrafluoroethanes involves reaction of hydrogen fluoride (i.e., HF) with tetrachloroethylene (i.e., $C_2Cl_4$) plus chlorine, or with its chlorine addition product, hexachloroethane (i.e., $C_2Cl_6$), in the liquid phase in the presence of an antimony pentahalide as catalyst. The $C_2Cl_3F_3$ and $C_2Cl_2F_4$ products consist predominantly of the more symmetrical isomers, that is, $CClF_2CCl_2F$ and $CClF_2CClF_2$, respectively (the symmetrical term referring to the distribution of the fluorine substituents in the molecule).

Since the boiling points of the two trichlorotrifluoroethanes and of the two dichlorotetrafluoroethanes differ only slightly from one another, separation by conventional distillation on a commercial scale is economically impractical. The lower-boiling dichlorotetrafluoroethanes (boiling range of about 3°–4° C.), however, are readily separable from the trichlorotrifluoroethanes (boiling range of about 46°–48° C.).

U.S. Pat. No. 5,055,624 discloses a process for the selective preparation of CFC-114a by fluorination of pure CFC-113a or mixtures of it with CFC-113 with anhydrous HF. The reaction is done in the liquid phase at 70° to 170° C., under pressure in the presence of an antimony compound of the formula $SbF_xCl_{5-x}$, where x is a number from 1 to 5. In Comparative Example 8, CFC-113 was reacted with HF under a preferred set of conditions at 151° C. to afford a product which contained 99.6 mole percent CFC-113 and 0.4 mole percent CFC-114. Example 4 discloses the reaction of CFC-113a with HF under similar conditions. A 99.7% yield of CFC-114a at 61.3% CFC-113a conversion was obtained.

The preparation of the trichlorotrifluoroethanes and the dichlorotetrafluoroethanes by vapor-phase reaction of HF with (A) $C_2Cl_4+Cl_2$ or (B) $CClF_2CCl_2F$ over a suitable catalyst at elevated temperatures has also been well-documented in the art. As disclosed in the art, the vapor-phase processes to the $C_2Cl_3F_3$ and $C_2Cl_2F_4$ compounds, whatever the catalyst employed, produce a mixture of the isomers.

European Patent Application Publication No. 317,981-A2 discloses a process for producing $CCl_2FCF_3$ which comprises isomerizing $CCl_2FCClF_2$ to form $CCl_3CF_3$, followed by fluorination with hydrogen fluoride. In the examples, the purest $CCl_2FCF_3$ obtained has a molar ratio of $CCl_2FCF_3$ to $CClF_2CClF_2$ of about 53:1. Also, in the examples the highest purity $CCl_3CF_3$ feed contains about 14% $CCl_2FCClF_2$ and 86% $CCl_3CF_3$.

There remains a need for processes to produce CFC-114a substantially free of its isomer, particularly processes which may employ conventional liquid-phase or vapor-phase fluorination techniques.

SUMMARY OF THE INVENTION

The present invention provides a process for producing a product comprising 1,1-dichlorotetrafluoroethane substantially free of 1,2-dichlorotetrafluoroethane. The process comprises the steps of: (i) contacting a mixture of perhalogenated hydrocarbons which is essentially free of 1,2-dichlorotetrafluoroethane and comprises from 20 to 80 mole percent 1,1,1-trichlorotrifluoroethane and from 5 to 80 mole percent total of at least one compound selected from the group consisting of tetrachloroethylene, pentachlorofluoroethane, tetrachloro-1,2-difluoroethane and tetrachloro-1,1-difluoroethane with hydrogen fluoride and optionally chlorine (provided that when the mixture comprises tetrachloroethylene, chlorine is supplied in a chlorine to tetrachloroethylene mole ratio of at least 1:2) over a fluorination catalyst at an elevated temperature no higher than 375° C., to provide a product mixture comprising 1,1,2-trichlorotrifluoroethane and dichlorotetrafluoroethane wherein the ratio of 1,2-dichlorotetrafluoroethane to 1,1-dichlorotetrafluoroethane is less than about 1:50; (ii) recovering said dichlorotetrafluoroethane from the product mixture; (iii) isomerizing 1,1,2-trichlorotrifluoroethane from the product mixture to 1,1,1-trichlorotrifluoroethane in the presence of an isomerization catalyst; and (iv) recycling the 1,1,1-trichlorotrifluoroethane produced by the isomerization of step (iii) to step (i).

The process may be used to produce high purity $CH_2FCF_3$ when combined with the hydrodehalogenation of the high purity CFC-114a from step (ii), (e.g., using a hydrogenation catalyst comprising a group VIII metal such as Pd supported on carbon or aluminum fluoride) in the presence of HF.

DETAILED DESCRIPTION

The process of this invention involves the simultaneous catalytic fluorination of $CF_3CCl_3$ and, at least one compound selected from the group consisting of $CCl_2=CCl_2$, $CCl_3CCl_2F$, $CCl_2FCCl_2F$, and $CCl_3CClF_2$. $CF_3CCl_2F$ substantially free of $CClF_2CClF_2$ is produced. In accordance with this invention the reaction temperature is maintained at an effective $CF_3CCl_3$ fluorination temperature that is below the temperature at which there is substantial fluorination of $CCl_2FCClF_2$ to $CClF_2CClF_2$ (i.e., a temperature no higher than about 375° C.). By such a process, $C_2Cl_2F_4$ containing a weight ratio of $CClF_2CClF_2$ to $CCl_2FCF_3$ of less than about 1:50 is readily produced and recovered. Under preferred conditions the $C_2Cl_2F_4$ isomer mixture produced contains less than 1 weight percent $CClF_2CClF_2$ and under more preferred conditions the $C_2Cl_2F_4$ contains less than 0.5 weight percent (5,000 ppm) $CClF_2CClF_2$, and under still more preferred conditions the $C_2Cl_2F_4$ contains less than 0.1 weight percent (1,000 ppm) $CClF_2CClF_2$. Further, the process substantially avoids overfluorination to $CClF_2CF_3$ (i.e., CFC-115) and $CF_3CF_3$ (i.e., FC-116).

While the fluorination reaction may be conducted in the liquid phase (e.g., using antimony catalysts at a temperature below 170° C.) the fluorination process is preferably conducted in the vapor phase at temperatures between 250° C. and 375° C. The fluorination process according no the present invention can be conducted batchwise, but is preferably conducted continuously in a manner generally known to the art for conducting catalyzed vapor-phase fluorination reactions.

CFC-113 may or may not be present in the mixture of halogenated hydrocarbons used in the fluorination step (step i). In a preferred embodiment, a perhalogenated hydrocarbon mixture fed to the fluorination step comprises CFC-113a and tetrachloroethylene, but has a CFC-113 content of less than about 10%, more preferably less than about 2%, and still more preferably less than about 1% by weight (e.g., about 0.1% by weight). Included are mixtures of $CCl_2=CCl_2$, $CCl_3CCl_2F$, $CCl_2FCCl_2F$ and/or $CCl_3CClF_2$ with $C_2Cl_3F_3$ product produced by the isomerization of $CClF_2CCl_2F$ to $CF_3CCl_3$ as described in the art (e.g., using an aluminum chloride catalyst as disclosed in Example I of U.S. Pat. No. 2,598,411). Many aluminum trihalide catalysts can be employed for such $CClF_2CCl_2F$ isomerization. A preferred catalyst is an anhydrous aluminum trichloride which has been micropulverized (i.e., mechanically comminuted by crushing, ball milling, rod milling, grinding or the like) to provide a surface area of greater than about 0.8 m²/g and has been activated by treatment under agitation with at least about 10 g of $CCl_2FCClF_2$ per g of aluminum trichloride. Reference is made to copending U.S. patent application Ser. No. 08/117,379 for further discussion of such isomerization.

Suitable vapor-phase fluorination catalysts include catalysts comprising trivalent chromium. In addition to a catalytically effective amount of trivalent chromium, such fluorination catalysts can include other components to increase catalyst activity and/or life such as one or more divalent metal cations (e.g., zinc, magnesium and/or and cobalt). The trivalent chromium catalyst may be unsupported (e.g., $Cr_2O_3$) or supported (e.g., on alumina, aluminum fluoride, magnesium fluoride or carbon).

Suitable vapor-phase fluorination catalysts include trivalent chromium halides (e.g., $CrCl_3$ and/or $CrF_3$) supported on carbon. A preferred catalyst is $CrF_3$ on carbon and is disclosed in U.S. Pat. No. 3,632,834, the contents of which are incorporated herein by reference. While any suitable carbon support may be used, a preferred carbon support is acid-washed prior to depositing trivalent chromium on it. Suitable trivalent chromium catalysts may be prepared by treating the carbon used as catalyst support with an acid, preferably with two acids. Typically the support is washed with deionized water after acid treatment and dried; and the chromium halide is then deposited thereon using deposit techniques well known in the art (see e.g., Example 1 of U.S. Pat. No. 3,632,834). Preferably, the chromium content (expressed as $CrCl_3$) is from about 5 to 50 weight percent of the carbon supported catalyst.

Acid treatment typically uses an acid other than hydrofluoric acid. Preferred acids used for the acid treatment contain neither phosphorus nor sulfur. Examples of acids which may be used in the first acid wash during the catalyst preparation process include organic acids such as acetic acid and inorganic acids such as HCl or $HNO_3$. Preferably hydrochloric acid or nitric acid is used. The second acid treatment, when employed, advantageously uses hydrofluoric acid. Normally, the carbon is treated with acid such that after such treatment the carbon contains less than about 0.1% by weight ash.

Commercially available carbons which may be treated with acids to provide suitable supports include those sold under the following trademarks: Darco™, Nuchar™, Columbia SBV™, Columbia MBV™, Columbia MBQ™, Columbia JXC™, Columbia CXC™, Calgon PCB™, Norit™ and Barnaby Cheny NB™. The carbon support can be in the form of powder, granules, extrudates, or pellets, etc.

The acid treatment may be accomplished in several ways. A suitable procedure is as follows. A carbon support is soaked overnight with gentle stirring in a 1 molar solution of the acid prepared in deionized water. The carbon support is then separated and washed with deionized water until the pH of the washings is about 3. Preferably, the carbon support is then soaked again with gentle stirring in a 1 molar solution of the acid prepared in deionized water for 12 to 24 hours. The carbon support is then finally washed with deionized water until the washings are substantially free of the anion of the acid (e.g., $Cl^-$ or $NO_3^-$), when tested by standard procedures. The carbon support is then separated and dried at about 120° C.. The washed carbon is then soaked, if necessary, in 1 molar HF prepared in deionized water for about 48 hours at room temperature with occasional stirring. The carbon support is separated and washed repeatedly with deionized water until the pH of the washings is greater than 4. The carbon support is then dried followed by calcination at about 300° C. for about 3 hours in air prior to its use as a support. Reference is made to U.S. Pat. No. 5,136,113 for further details relating to producing acid-washed carbon catalysts.

The halogenated hydrocarbon feed comprises 20 to 80 mole percent $CCl_3CF_3$ and 5 to 80 mole percent of at least one compound selected from the group consisting of $CCl_2=CCl_2$, $CCl_3CCl_2F$, $CCl_2FCCl_2F$, and $CCl_3CClF_2$. The mole ratio of HF to the total of $CCl_3CF_3$, $CCl_2=CCl_2$, $CCl_3CCl_2F$, $CCl_2FCCl_2F$ and $CCl_3CClF_2$ can vary widely, but should be at least stoichiometric. The preferred ratio is from about 2:1 to about 10:1. When chlorine is supplied to the reaction mixture it is typically added in limited amounts such that less than 1000 ppm chlorine is in the reactor effluent.

The reaction temperature (which will be below the temperature at which $CClF_2CCl_2F$ is fluorinated to $CClF_2CClF_2$ in the presence of hydrogen fluoride, the fluorination catalyst and optionally chlorine) will normally be below about 375° C. but, for a vapor-phase reaction, at least about 250° C. Preferably, the reaction temperature for vapor-phase reactions is in the range of from about 300° C. to about 350°

C. At temperatures lower than about 250° C., the CFC-114a production rate is lower than desired, at temperatures higher than about 375° C., greater than desired amounts of CFC-114 begin to be observed.

Pressure is not critical. Atmospheric and superatmospheric pressures (e.g., from about 100 kPa to about 7000 kPa) are the most convenient and are therefore preferred.

For continuous processes the fluorination reaction is generally conducted in a reaction zone for the fluorination. The reaction zone may contain more than one reactor, multiple feed lines, as well as interstage cooling or heating, addition of reactants, diluents, recycle streams, etc. For example, multiple reactors may be used to stage the degree of fluorination so that undue temperature rise and overfluorination are avoided. The reaction product is normally recovered at the end of the reaction zone. If necessary, the reaction products, intermediates and/or by-products can be removed at various stages of the reaction zone and if desired, recycled to different parts of the reaction zone. For example, HF and CFC-113a can be fed to a reaction zone at more than one feed location. CFC-114a is generally recovered from the end of the reaction zone.

The reaction product stream can be treated in accordance with any of the techniques known to the art for separating the desired fluorination product from other compounds which might be present such as by-product hydrogen chloride, unreacted hydrogen fluoride, unreacted chlorine gas (if used), pentachlorofluoroethane, tetrachlorodifluoroethanes, trichlorotrifluoroethanes and other minor by-products (e.g., chloropentafluoroethane). For example $C_2Cl_2F_4$ (which is almost entirely CFC-114a) can be separated from the other components of the reaction products by conventional methods such as distillation. It has been found that during this separation CFC-114a can form a binary azeotrope with HF. (See U.S. patent application Ser. No. 08/146,862 for further discussion of $HF/CF_3CCl_2F$ azeotropes). Accordingly, the $C_2Cl_2F_4$ can be recovered as a composition consisting essentially of an azeotrope of CFC-114a and HF, using distillation.

Alternatively, the product stream may be scrubbed with water or aqueous alkali to remove hydrogen halides and chlorine, dried with a drying agent, such as silica gel or a molecular sieve adapted to such purpose, then condensed and recovered. The dichlorotetrafluoroethane product, consisting essentially of the 1,1-dichloro isomer substantially free of the 1,2-dichloro isomer, is readily separated from any trichlorotrifluoroethanes by distillation in view of the substantial difference in their boiling points. The trichlorotrifluoroethanes can be recycled to the reactor, if desired. The bottom products of the distillation column, which might contain for example, $CCl_3CCl_2F$, $CCl_2FCCl_2F$, $CCl_3CClF_2$, $CCl_2FCClF_2$, $CCl_3CF_3$, and unreacted $CCl_2=CCl_2$, can be fed to another distillation column to remove $CCl_2=CCl_2$. It has been found that during this distillation CFC-113a can form a binary azeotrope as well as possibly ternary azeotropes with HF and other distillation column products. (See U.S. patent application Ser. No. 08/146,862 for further discussion of the CFC-113a/HF azeotrope).

After $CCl_2=CCl_2$ removal, the other chlorofluorocarbons from the bottom products may be fed to an isomerization zone (e.g., such as described in U.S. Pat. No. 2,598,411) where $CCl_2FCCl_2F$ may be isomerized to $CCl_3CClF_2$ and $CCl_2FCClF_2$ may be isomerized to $CCl_3CF_3$. HF should be removed from the chlorofluorocarbons prior to being fed to the isomerization zone. The isomerization zone effluent can then be recycled back to the reaction zone.

CFC-114a and/or the CFC-114a/HF azeotrope can be hydrodehalogenated using the procedures and catalysts disclosed in U.S. Pat. No. 5,136,113 (the entire contents of which are hereby incorporated by reference), using the procedures disclosed in PCT International Publication No. WO91/05752, or using other methods known in the art. In accordance with the present invention the $C_2Cl_2F_4$ recovered as a composition consisting essentially of an azeotrope of CFC-114a and HF can be hydrodehalogenated in the presence of the HF from said azeotropic compositions to produce $CH_2FCF_3$ as a major product. HF which originated from the CFC-114a azeotrope can then be removed along with any additional HF produced by the hydrodehalogenation. If desired, CFC-114a may be separated from HF by conventional means such as neutralization followed by decantation in order to obtain pure CFC-114a.

The reactors and their associated feed lines, effluent lines and associated units should be constructed of materials resistant to hydrogen fluoride, hydrogen chloride and chlorine. Typical materials of construction, well-known to the fluorination art, include stainless steels, in particular of the austenitic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluorochloroethylene and polytetrafluoroethylene, generally used as linings.

Processes for producing CFC-114a from CFC-113a by catalytic fluorination with HF can result in reactor effluent containing CFC-113a, CFC-114a, and HF. Separation of such effluent can result in production of both CFC-114a/HF and CFC-113a/HF azeotropes. The CFC-113a/HF azeotrope is useful as feed to produce additional CFC-114a. The CFC-114a/HF azeotrope is useful as feed to produce CFC-115. Processes for producing CFC-115 from CFC-114a by catalytic fluorination with HF can result in reactor effluent containing CFC-114a, CFC-115, and HF. Separation of such effluent can result in production of the 114a/HF azeotrope. As noted above, the CFC-114a/HF azeotrope is useful as feed for producing additional CFC-115. The CFC-115 and HF are useful as feed to produce CFC-116 by catalytic fluorination of CFC-115 with HF. It will also be apparent to one of ordinary skill in the art that distillation including azeotropes with HF can typically be run under more convenient conditions than distillation without HF (e.g., where HF is removed prior to distillation).

Practice of the invention will become further apparent from the following non-limiting examples.

EXAMPLES

Activation Procedure

A ⅝" (1.58 cm) I.D. Inconel® nickel alloy reactor was charged with a catalyst and heated to 300° C. in a flow of nitrogen (25 mL/min) for about 20 hours. The temperature was reduced to 175° C. and a 2:1 molar ratio of nitrogen and HF was started through the reactor (total flow 100 mL/min). After one hour under these conditions, the molar ratio of nitrogen to HF was adjusted to 1:3 and the temperature increased gradually over a two hour period to 400° C. The reactor was then brought back to the desired operating temperature, the nitrogen flow stopped, and the flow of reactants started.

Analytical Procedure

The reactor effluent was sampled on-line with a Hewlett Packard HP 5890 gas chromatograph using a 20 foot (6.1 m)

long, one-eighth inch (0.32 cm) diameter, column containing Krytox™ perfluorinated polyether on an inert support and a helium flow of 35 mL/min. Gas chromatographic conditions were 70° C. for three minutes followed by temperature programming to 180° C. at a rate of 6° C./minute. The table percentages are in mole%.

EXAMPLE 1

Chlorofluorination of a Mixture of Tetrachloroethylene and 1,1,1-Trichlorotrifluoroethane The reactor was charged with a 29% $CrCl_3$/carbon (30 mL, 10.2 g) catalyst and the catalyst was activated according to the Activation Procedure above. The reaction temperature was 350° C. and the contact time was 30 seconds. The reaction effluent was analyzed according to the Analytical Procedure above. The $CF_3CCl_3$ (CFC-113a) feed was 99.99% pure. In all cases no $CClF_2CClF_2$ was detected. The detection limit for CFC-114 was about 1000 ppm. The products also included $CClF_2CF_3$ (CFC-115) which was found to be present in less than 1000 ppm. The chlorofluorination results are shown in Table 1.

TABLE 1

| Time (hours) | Molar Ratio HF/PCE/113a/Cl$_2$ | 114a[a] | 113[b] | 113a[c] | 112/a[d] | 111[e] | PCE[f] |
|---|---|---|---|---|---|---|---|
| 8 | 4/1/1/0.75 | 16.9 | 7.8 | 29.9 | 34.4 | 3.1 | 7.1 |
| 15 | 4/1/1/1 | 14.1 | 6.5 | 33.5 | 40.6 | 5.0 | 0.2 |
| 22 | 4/1/1/1 | 11.5 | 5.2 | 35.0 | 39.2 | 5.5 | 3.4 |
| 29 | 4/1/1/1 | 12.1 | 5.5 | 35.8 | 41.4 | 4.9 | 0.3 |
| 74 | 4/1/1/1 | 20.0 | 2.5 | 27.9 | 38.0 | 9.5 | 2.0 |
| 79 | 6/1/1/1.5 | 26.2 | 3.8 | 21.0 | 42.2 | 6.4 | 0.2 |
| 90 | 6/1/1/1.5 | 29.8 | 4.7 | 20.6 | 40.6 | 4.1 | 0.1 |
| 100 | 6/1/1/1.5 | 29.4 | 4.8 | 19.1 | 42.8 | 3.9 | <0.1 |
| 108 | 16/3/1/4 | 13.3 | 8.6 | 7.1 | 66.2 | 4.7 | <0.1 |

[a]114a is $CF_3CCl_2F$
[b]113 is $CCl_2FCClF_2$
[c]113a is $CF_3CCl_3$
[d]112/a is $CCl_2FCCl_2F + CCl_3CClF_2$
[e]111 is $CCl_3CCl_2F$
[f]PCE is $CCl_2=CCl_2$

EXAMPLE 2

Fluorination of a Mixture of 1,1,1,2-Tetrachlorodifluoroethane and 1,1,1-Trichlorotrifluoroethane The reactor was charged with a 29% $CrCl_3$/carbon (30 mL, 12.9 g) catalyst and the catalyst was activated according to the Activation Procedure above. The reaction temperature was varied from 275° to 350° C. as shown in Table 2, the HF: (112a+113a) ratio was 2:1, and the contact time was 30 seconds. The feed contained the following components (mole %): 71.1% $CCl_3CF_3$, 24.0% $CCl_3CClF_2$, 3.8% $C_2Br_2ClF_3$, 0.47% $CCl_2FCF_3$, 0.32% $C_3BrCl_2F_5$ and 0.15% $CCl_2FCClF_2$. The molar ratio of $CCl_3CClF_2$ (CFC-112a) to $CCl_3CF_3$ was 1:3. The reaction effluent was analyzed according to the Analytical Procedure above. The detection limit for CFC-114 was about 1000 ppm. The fluorination results are shown in Table 2.

TABLE 2

| Time (hours) | Temp. (°C.) | 115 | 114[a] | 114a | 113 | 113a | 112a[b] |
|---|---|---|---|---|---|---|---|
| 0 | — | 0.0 | 0.0 | 0.5 | 0.2 | 71.1 | 24.0 |
| 4 | 275 | 0.0 | 0.0 | 16.2 | 15.9 | 56.8 | 7.8 |
| 7 | 300 | 0.2 | 0.1 | 41.7 | 21.9 | 31.9 | 1.5 |
| 10 | 325 | 0.5 | 0.5 | 60.6 | 21.0 | 13.2 | 1.1 |
| 13 | 350 | 1.2 | 1.2 | 66.9 | 19.0 | 7.2 | 1.3 |

[a]114 is $CClF_2CClF_2$
[b]112a is $CCl_3CClF_2$

The reactor products also contained minor amounts of the following compounds: $CHF_3$, $CClF_3$, $CBrF_3$, $CHCl_2CF_3$, $C_2BrClF_4$, $C_2BrCl_2F_3$, $C_2Br2ClF_3$, and $C_3BrCl_2F_5$.

EXAMPLE 3

Hydrodechlorination of $CCl_2FCF_3$/HF Mixtures

A 6" (15.2 cm)×⅝" (1.58 cm) O.D. Inconel™ nickel alloy reactor was charged with 0.5% Pd on acid-washed carbon catalyst (11.5 g, 30 mL). The reactor contents were heated to a temperature of 150° C. overnight in a flow of 10 cc/min of nitrogen. At the end of this period, nitrogen flow was stopped, and a hydrogen flow of 25 cc/min was started and maintained for 24 hours. After this period, the reaction of CFC-114a, HF and $H_2$ was started.

The $CCl_2FCF_3$ hydrogenolysis was done under the following conditions: a reaction temperature of 158° C., atmospheric pressure, a $H_2$:$CCl_2FCF_3$:HF molar ratio of about 2:1:0.25, and a contact time of 15 seconds.

The products leaving the reactor were analyzed on line using a gas chromatograph. The column consisted of a 20' (6.1 m)×⅛" (0.32 mm) stainless steel tube containing Krytox™ perfluorinated polyether on an inert support. Helium was used as the carrier gas. The product analyses are reported in mole % and are shown in Table 3.

TABLE 3

| Hours on Stream | % 114a | 124[a] | 134a[b] | 143a[c] |
|---|---|---|---|---|
| 0.5 | 2.3 | 24.8 | 69.5 | 3.4 |
| 1.5 | 39.1 | 16.1 | 42.6 | 2.3 |
| 2.0 | 39.9 | 15.1 | 42.8 | 2.2 |
| 3.0 | 41.3 | 14.2 | 42.3 | 2.2 |

TABLE 3-continued

| Hours on Stream | % 114a | 124[a] | 134a[b] | 143a[c] |
|---|---|---|---|---|
| 4.0 | 43.1 | 13.6 | 41.1 | 2.2 |
| 5.0 | 43.6 | 12.8 | 41.6 | 2.0 |
| 5.5 | 44.2 | 12.4 | 41.4 | 2.0 |
| 6.0 | 44.4 | 12.2 | 41.4 | 2.0 |

[a] 124 is $CF_3CHClF$
[b] 134a ia $CF_3CH_2F$
[c] 143a is $CF_3CH_3$

I claim:

1. A process for producing a product comprising 1,1-dichlorotetrafluoroethane substantially free of 1,2-dichlorotetrafluoroethane, comprising the steps of:

(i) contacting a mixture of perhalogenated hydrocarbons which is essentially free of 1,2-dichlorotetrafluoroethane and comprises from 20 to 80 mole percent 1,1,1-trichlorotrifluoroethane and from 5 to 80 mole percent of at least one compound selected from the group consisting of tetrachloroethylene, pentachlorofluoroethane, tetrachloro-1,2-difluoroethane and tetrachloro-1,1-difluoroethane with hydrogen fluoride and optionally chlorine, provided that when chlorine is present contact is in the vapor phase and when the mixture comprises tetrachloroethylene chlorine is supplied in a chlorine to tetrachloroethylene mole ratio of at least 1:2, over a fluorination catalyst at an elevated temperature no higher than 375° C., to provide a product mixture comprising 1,1,2-trichlorotrifluoroethane and dichlorotetrafluoroethane wherein the ratio of 1,2-dichlorotetrafluoroethane to 1,1-dichlorotetrafluoroethane is less than about 1:50;

(ii) recovering said dichlorotetrafluoroethane from the product mixture;

(iii) isomerizing 1,1,2-trichlorotrifluoroethane from the product mixture to 1,1,1-trichlorotrifluoroethane in the presence of an isomerization catalyst, said isomerization catalyst being an aluminum trihalide catalyst prepared by micropulverizing an anhydrous aluminum trichloride to provide a surface area of greater than about 0.8 $m^2/g$ and activating by treatment under agitation with at least about 10 grams of $CCl_2FCClF_2$ per gram of aluminum trichloride; and (iv) recycling the 1,1,1-trichlorotrifluoroethane produced by the isomerization of step (iii) to step (i).

2. The process of claim 1 wherein the fluorination of step (i) is conducted in the vapor phase at a temperature between 250° C. and 375° C.

3. The process of claim 2 wherein the fluorinating catalyst of step (i) comprises trivalent chromium.

4. The process of claim 2 wherein the mixture of halogenated hydrocarbons used in step (i) contains less than about 10% by weight $CClF_2CCl_2F$.

5. The process of claim 2 wherein the $C_2Cl_2F_4$ isomer mixture produced contains less than one weight percent $CClF_2CClF_2$.

6. A process for producing $CH_2FCF_3$ by hydrodehalogenating $CCl_2FCF_3$ characterized by:

(i) contacting a mixture of perhalogenated hydrocarbons which is essentially free of 1,2-dichlorotetrafluoroethane and comprises 20 to 80 mole percent 1,1,1-trichlorotrifluoroethane and 5 to 80 mole percent of at least one compound selected from the group consisting of tetrachloroethylene, pentachlorofluoroethane, tetrachloro-1,2-difluoroethane and tetrachloro-1,1-difluoroethane with hydrogen fluoride and optionally chlorine, provided that when chlorine is present contact is in the vapor phase and when the mixture comprises tetrachloroethylene, chlorine is supplied in a chlorine to tetrachloroethylene mole ratio of at least 1:2, over a fluorination catalyst at an elevated temperature no higher than 375° C., to provide a product mixture comprising 1,1,2-trichlorotrifluoroethane and dichlorotetrafluoroethane wherein the ratio of 1,2-dichlorotetrafluoroethane to 1,1-dichlorotetrafluoroethane is less than about 1:50;

(ii) recovering said dichlorotetrafluoroethane from the product mixture;

(iii) isomerizing 1,1,2-trichlorotrifluoroethane from the product mixture to 1,1,1-trichlorotrifluoroethane in the presence of an isomerization catalyst, said isomerization catalyst being an aluminum trihalide catalysts prepared by micropulverizing an anhydrous aluminum trichloride to provide a surface area of greater than about 0.8 $m^2/g$ and activating by treatment under agitation with at least about 10 grams of $CCl_2FCClF_2$ per gram of aluminum trichloride and;

(iv) recycling the 1,1,1-trichlorotrifluoroethane produced by the isomerization of step (iii) to step (i); and (v) hydrodehalogenating the dichlorotetrafluoroethane from step (ii).

7. The process of claim 6 wherein in step (ii) the dichlorotetrafluoroethane is recovered as a composition consisting essentially of an azeotrope of 1,1-dichlorotetrafluoroethane and HF; and wherein the dichlorotetrafluoroethane is hydrodehalogenated in the presence of the HF from said azeotropic composition.

8. The process of claim 6 wherein the fluorination catalyst of step (i) comprises trivalent chromium.

9. A process for producing a product comprising 1,1-dichlorotetrafluoroethane substantially free of 1,2-dichlorotetrafluoroethane, comprising the steps of:

(i) contacting a mixture of perhalogenated hydrocarbons which is essentially free of 1,2-dichlorotetrafluoroethane and comprises from 20 to 80 mole percent 1,1,1-trichlorotrifluoroethane and from 5 to 80 mole percent of at least one compound selected from the group consisting of tetrachloroethylene, pentachlorofluoroethane, tetrachloro-1,2-difluoroethane and tetrachloro-1,1-difluoroethane with hydrogen fluoride and optionally chlorine, provided that when chlorine is present contact is in the vapor phase and when the mixture comprises tetrachloroethylene chlorine is supplied in a chlorine to tetrachloroethylene mole ratio of at least 1:2, over a fluorination catalyst comprising trivalent chromium at an elevated temperature no higher than 375° C., to provide a product mixture comprising 1,1,2-trichlorotrifluoroethane and dichlorotetrafluoroethane wherein the ratio of 1,2-dichlorotetrafluoroethane to 1,1-dichlorotetrafluoroethane is less than about 1:50;

(ii) recovering said dichlorotetrafluoroethane from the product mixture;

(iii) isomerizing 1,1,2-trichlorotrifluoroethane from the product mixture to 1,1,1-trichlorotrifluoroethane in the presence of an isomerization catalyst; and (iv) recycling the 1,1,1-trichlorotrifluoroethane produced by the isomerization of step (iii) to step (i).

10. The process of claim 9 wherein the mixture of perhalogenated hydrocarbons is contacted with hydrogen fluoride and optionally chlorine over a trivalent chromium halide supported on carbon.

11. The process of claim 10 wherein the trivalent chromium halide is $CrF_3$.

12. The process of claim 9 wherein the fluorination of step (i) is conducted in the vapor phase at a temperature between 250° C. and 375° C.

13. The process of claim 12 wherein the mixture of halogenated hydrocarbons used in step (i) contains less than about 10% by weight $CClF_2CCl_2F$.

14. The process of claim 12 wherein the $C_2Cl_2F_4$ isomer mixture produced contains less than one weight percent $CClF_2CClF_2$.

15. The process of claim 1 wherein the fluorination of step (i) is conducted in the vapor phase.

16. The process of claim 6 wherein the fluorination of step (i) is conducted in the vapor phase.

17. The process of claim 1 wherein in (i) the mole ratio of HF to the total of $CCl_3CF_3$, $CCl_2=CCl_2$, $CCl_3CCl_2F$, $CCl_2FCCl_2F$ and $CCl_3CClF_2$ is from about 2:1 to about 10:1 and the reaction temperature in (i) is maintained at an effective $CF_3CCl_3$ fluorination temperature that is below the temperature at which there is substantial fluorination of $CCl_2FCClF_2$ such that the product mixture provided in (i) comprises $C_2Cl_2F_4$ which contains less than 1 weight percent $CClF_2CClF_2$.

18. The process of claim 6 wherein in (i) the mole ratio of HF to the total of $CCl_3CF_3$, $CCl_2=CCl_2$, $CCl_3CCl_2F$, $CCl_2FCCl_2F$ and $CCl_3CClF_2$ is from about 2:1 to about 10:1 and the reaction temperature in (i) is maintained at an effective $CF_3CCl_3$ fluorination temperature that is below the temperature at which there is substantial fluorination of $CCl_2FCClF_2$ such that the product mixture provided in (i) comprises $C_2Cl_2F_4$ which contains less than 1 weight percent $CClF_2CClF_2$.

19. The process of claim 9 wherein in (i) the mole ratio of HF to the total of $CCl_3CF_3$, $CCl_2=CCl_2$, $CCl_3CCl_2F$, $CCl_2FCCl_2F$ and $CCl_3CClF_2$ is from about 2:1 to about 10:1 and the reaction temperature in (i) is maintained at an effective $CF_3CCl_3$ fluorination temperature that is below the temperature at which there is substantial fluorination of $CCl_2FCClF_2$ such that the product mixture provided in (i) comprises $C_2Cl_2F_4$ which contains less than 1 weight percent $CClF_2CClF_2$.

\* \* \* \* \*